US012673118B2

(12) United States Patent
Piao et al.

(10) Patent No.: US 12,673,118 B2
(45) Date of Patent: Jul. 7, 2026

(54) DEVELOPMENT OF DUAL-GRNA APPROACH WITH UNDETECTABLE OFF-TARGET EFFECT TO CORRECT C9ORF72 REPEAT EXPANSION AND C9ORF72 PATHOLOGY

(71) Applicant: TSINGHUA UNIVERSITY, Beijing (CN)

(72) Inventors: Xuejiao Piao, Beijing (CN); Yichang Jia, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 964 days.

(21) Appl. No.: 17/788,670

(22) PCT Filed: Dec. 23, 2019

(86) PCT No.: PCT/CN2019/127553
§ 371 (c)(1),
(2) Date: Jun. 23, 2022

(87) PCT Pub. No.: WO2021/127886
PCT Pub. Date: Jul. 1, 2021

(65) Prior Publication Data
US 2023/0040053 A1 Feb. 9, 2023

(51) Int. Cl.
*A61K 48/00* (2006.01)
*A61K 31/7088* (2006.01)
*A61K 38/46* (2006.01)
*A61P 25/28* (2006.01)
*C12N 9/22* (2006.01)
*C12N 15/11* (2006.01)

(52) U.S. Cl.
CPC ...... *A61K 48/0066* (2013.01); *A61K 31/7088* (2013.01); *A61K 38/465* (2013.01); *A61P 25/28* (2018.01); *C12N 9/22* (2013.01); *C12N 15/11* (2013.01)

(58) Field of Classification Search
CPC ...... C12N 2310/20; C12N 2740/15043; C12N 2750/14143; C12N 15/113; C12N 15/11; C12N 2320/53; A61K 48/0066; A61K 31/7088; A61K 48/0058; A61K 48/005; A61P 25/28
See application file for complete search history.

(56) References Cited

U.S. PATENT DOCUMENTS

| | | | |
|---|---|---|---|
| 10,407,678 | B2 | 9/2019 | Rigo |
| 2018/0094267 | A1 | 4/2018 | Heslin et al. |
| 2019/0249230 | A1 | 8/2019 | Pederson et al. |

FOREIGN PATENT DOCUMENTS

| | | | | |
|---|---|---|---|---|
| WO | WO-2015089351 A1 * | 6/2015 | ......... | A01K 67/0276 |
| WO | WO 2016/167780 A1 | 10/2016 | | |
| WO | WO 2017/040813 A2 | 3/2017 | | |
| WO | WO-2017109757 A1 * | 6/2017 | .......... | A61K 31/395 |
| WO | WO-2018064600 A1 * | 4/2018 | ......... | A01K 67/0278 |

OTHER PUBLICATIONS

Pribadi, CRISPR-Cas9 targeted deletion of the C9orf72 repeat expansion mutation corrects cellular phenotypes in patient-derived iPS cells. bioRxiv, May 2, 2016.*
Meijboom, CRISPR Cas9-mediated excision of ALS FTD-causing hexanucleotide repeat expansion in C9ORF72 rescues major disease mechanisms in vivo and in vitro. Nature Communications 13:6286 (Year: 2022).*
Kempthorne, Dual-targeting CRISPR-CasRx reduces C9orf72 ALS FTD sense and antisense repeat RNAs in vitro and in vivo. Nature Communications 16:459 (Year: 2025).*
International Search Report issued on Sep. 25, 2020 in PCT/CN2019/127553 filed on Dec. 23, 2019, citing references, 6 pages.
Selvaraj et al., "C9ORF72 repeat expansion causes vulnerability of moto neurons to Ca²⁺-permeable AMPA receptor-mediated excitotoxicity", Nature Communications, 2018, vol. 9, pp. 1-14.
Pribadi et al., "CRISPR-Cas9 targeted deletion of the C9orf72 repeat expansion mutation corrects cellular phenotypes in patient-derived iPS cells", Biorxiv Preprint, 2016, pp. 1-32.
Zhang et al., "C9ORF72 Mutation in FTD-ALS: Genetics, Pathogenesis, Clinical Feature and Therapy", Chin. J. Clin. Neurosci., 2019, vol. 27, No. 5, pp. 559-564 (with English Abstract).

* cited by examiner

*Primary Examiner* — Jennifer Dunston
*Assistant Examiner* — Julio Washington Gomez Rodriguez
(74) *Attorney, Agent, or Firm* — Merchant & Gould P.C.; Daniel J. Pereira

(57) ABSTRACT

A group of gRNAs is provided, and the group of gRNAs comprises a first gRNA molecule; and a second gRNA molecule capable of defining a region in a genome sequence with the first gRNA molecule, wherein the region in the genome comprises a target sequence in need of removal.

11 Claims, 6 Drawing Sheets

Specification includes a Sequence Listing.

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial
<220> FEATURE:
<223> OTHER INFORMATION: gRNA1

<400> SEQUENCE: 1
tgctctcaca gtactcgctg agg                                          23

<210> SEQ ID NO 2
<211> LENGTH: 23
<212> TYPE: DNA
<213> ORGANISM: Artificial
<220> FEATURE:
<223> OTHER INFORMATION: gRNA2

<400> SEQUENCE: 2
gggctttcgc ctctagcgac tgg                                          23

<210> SEQ ID NO 3
<211> LENGTH: 23
<212> TYPE: DNA
<213> ORGANISM: Artificial
<220> FEATURE:
<223> OTHER INFORMATION: gRNA3

<400> SEQUENCE: 3
ccgcagcctg tagcaagctc tgg                                          23

<210> SEQ ID NO 4
<211> LENGTH: 23
<212> TYPE: DNA
<213> ORGANISM: Artificial
<220> FEATURE:
<223> OTHER INFORMATION: gRNAb

<400> SEQUENCE: 4
ggcccgcccc gaccacgccc cgg                                          23
```

DEVELOPMENT OF DUAL-GRNA APPROACH WITH UNDETECTABLE OFF-TARGET EFFECT TO CORRECT C9ORF72 REPEAT EXPANSION AND C9ORF72 PATHOLOGY

FIELD

The present invention relates to biotechnology, especially to an isolated nucleic acid molecule, a pair of gRNA, a construct, a kit, a method of correcting C9ORF72 repeat expansion, a therapeutic composition for treating C9ORF72 related disease and a method for treating C9ORF72 related disease.

BACKGROUND

C9ORF72 GGGGCC repeat expansion is the most common genetic cause for both ALS (Amyotrophic lateral sclerosis) and FTD (frontotemporal dementia). The repeat expansion causes disease probably through multiple paths. At DNA level, GGGGCC repeats form G-quadruplex to decrease C9ORF72 expression. At RNA level, transcribed RNAs from the expansion form RNA foci to sequester RNA-binding proteins and disrupt their functions.

At protein level, sense and antisense repeat RNAs produce toxic dipeptide repeat proteins. So far, no available therapeutic approach targets these three pathogenic aspects at a time. Recently, efficacy of CRISPR (clustered regularly interspaced short palindromic repeats)/Cas9 has been proven in treatment of human disease.

SUMMARY

Here the inventor establishes a dual-gRNA-mediated deletion approach to remove the repeat DNA with ~50% efficiency but has little effect on C9ORF72 protein expression. In neurons carrying human C9ORF72 repeat expansion, the approach removes the repeat DNA in vitro and in vivo. In addition, in agreement with high repeat DNA removal efficiency, the designed gRNAs correct the RNA foci with high efficacy in vitro and in vivo. Using a sensitive, unbiased, and genome-wide off-target detector, experimentally the inventor demonstrated the approach has no detectable off-target effect. Therefore, the prototype research provides a one-time treatment solution to permanently remove C9ORF72 repeat DNA with a high efficiency, which potentially corrects both repeat-mediated RNA and protein abnormities at the same time.

In one aspect of present disclosure, a group of gRNAs is provided, and according to embodiments of present disclosure, the group of gRNAs comprises a first gRNA molecule; and a second gRNA molecule capable of defining a region in a genome sequence with the first gRNA molecule, wherein the region in the genome comprises a target sequence in need of removal. The group of gRNAs can remove the region in the genome comprises a target sequence with a high efficiency, which potentially corrects both RNA and protein abnormities at the same time.

According to embodiments of present disclosure, the above mentioned group of gRNAs may possess at least one of the following additional features:

According to embodiments of present disclosure, the target sequence has an GC content of at least 80%.

According to embodiments of present disclosure, the target sequence consisting of at least one of G and C.

According to embodiments of present disclosure, the target sequence has at least of two GGGGCC repeats.

According to embodiments of present disclosure, if the target sequence is located in a non-coding sequence in the genome, a sequence corresponding to the first or second gRNA molecule in the genome is also located in a non-coding sequence.

According to embodiments of present disclosure, the target sequence is located between the first exon and the second exon, wherein the first exon and the second exon are the exons nearest to the target sequence, and the first exon is located upstream of the target sequence, and the second exon is located downstream of the target sequence.

According to embodiments of present disclosure, the first gRNA molecule is set between the first exon and the target sequence, the second gRNA molecule is set between the target sequence and the second exon.

According to embodiments of present disclosure, the first gRNA molecule is set between the first exon and the target sequence, the second gRNA molecule is set downstream of the second exon but upstream of initiation codon.

According to embodiments of present disclosure, the second gRNA molecule is set nearby the second exon, for example, the length between the second gRNA molecule and the second exon is at most 200 bp.

According to embodiments of present disclosure, wherein the first gRNA molecule comprises a nucleic acid sequence of SEQ ID NO:1 (shown as gRNA1) or SEQ ID NO:3 (shown as gRNA3); and a second gRNA molecule comprises a nucleic acid sequence of SEQ ID NO: 2 (shown as gRNA2) or SEQ ID NO:4 (shown as gRNAb).

```
                                        (SEQ ID NO: 1)
        TGCTCTCACAGTACTCGCTGAGG.

(SEQ ID NO: 2)
        GGGCTTTCGCCTCTAGCGACTGG.

(SEQ ID NO: 3)
        CCGCAGCCTGTAGCAAGCTCTGG.

(SEQ ID NO: 4)
        GGCCCGCCCCGACCACGCCCCGG.
```

According to embodiments of present disclosure, wherein the first gRNA molecule comprises a nucleic acid sequence of SEQ ID NO: 1; and a second gRNA molecule comprises a nucleic acid sequence of SEQ ID NO: 2. The inventor surprisely found that the group gRNA comprising the first gRNA molecule and the second gRNA molecule can remove the repeat DNA with ~50% efficiency but has little effect on C9ORF72 protein expression.

In the second aspect of present disclosure, a construct is provided, and according to embodiments of present disclosure, the construct comprises a sequence encoding the group of gRNAs described above.

According to embodiments of present disclosure, the above mentioned construct may possess at least one of the following additional features:

According to embodiments of present disclosure, the construct further comprising: a first promoter operably linked to the first nucleic acid molecule encoding the first gRNA molecule; and a second promoter operably linked to the second nucleic acid molecule encoding the second gRNA molecule.

According to embodiments of present disclosure, each of the first and second promoters comprises at least one selected independently from a group consisting of U6, H1, CMV, EF-1, RSV, and LTR promoters respectively.

According to embodiments of present disclosure, the construct is a non-pathogenic virus. According to embodiments of present disclosure, the construct is a virus selected from a retrovirus, lentivirus, adenovirus, adenovirus and AAV.

In the third aspect of present disclosure, a kit is provided, and according to embodiments of present disclosure, the kit comprises: the construct described above; or the group of gRNAs described above.

According to embodiments of present disclosure, the above mentioned kit may possess at least one of the following additional features:

According to embodiments of present disclosure, the kit further comprising the isolated nucleic acid molecule encoding a nuclease, wherein the nuclease can target specific genome sequence as a genome editing tool.

According to embodiments of present disclosure, wherein the nuclease including CRISPR(Clustered Regularly Interspaced Short Palindromic Repeats)/Cas9.

In the fourth aspect of present disclosure, a method of modifying a cell is provided, and according to embodiments of present disclosure, the method comprises introducing the construct described above, or the group of gRNAs described above into the cell in need of modification.

According to embodiments of present disclosure, the method further comprising the step of introducing a sequence encoding a nuclease, wherein the nuclease can target specific genome sequence as a genome editing tool.

According to embodiments of present disclosure, the cell comprises a sequence encoding a nuclease, wherein the nuclease can target specific genome sequence as a genome editing tool.

According to embodiments of present disclosure, wherein the nuclease including CRISPR/Cas9.

In the fifth aspect of present disclosure, a method of correcting C9ORF72 repeat expansion for cells is provided, and according to embodiments of present disclosure, the method comprises introducing the construct described above, or the group of gRNAs described above into the cells.

According to embodiments of present disclosure, the method further comprising the step of introducing a sequence encoding a nuclease, wherein the nuclease can target specific genome sequences a genome editing tool.

According to embodiments of present disclosure, the cell comprises a sequence encoding a nuclease, wherein the nuclease can target specific genome sequence as a genome editing tool.

According to embodiments of present disclosure, the nuclease including CRISPR/Cas9.

In the sixth aspect of present disclosure, a therapeutic composition for treating C9ORF72 related disease is provided. According to embodiments of present disclosure, the therapeutic composition comprises: the construct, or the group of gRNAs described above.

According to embodiments of present disclosure, the therapeutic composition further comprising pharmaceutically acceptable adjuvant.

According to embodiments of present disclosure, the therapeutic composition is in the form of injection.

In the seventh aspect of present disclosure, a method for treating C9ORF72 related disease is provided. According to embodiments of present disclosure, the method comprise: administrating the construct, or the group of gRNAs describe above to a patient in need of such treatment.

According to embodiments of present disclosure, the method further comprises administrating the isolated nucleic acid molecule encoding a nuclease, wherein the nuclease can target specific genome sequence as a genome editing tool.

According to embodiments of present disclosure, the nuclease including CRISPR/Cas9.

According to embodiments of present disclosure, the C9ORF72 related disease comprising ALS or FTD.

Figure 2:
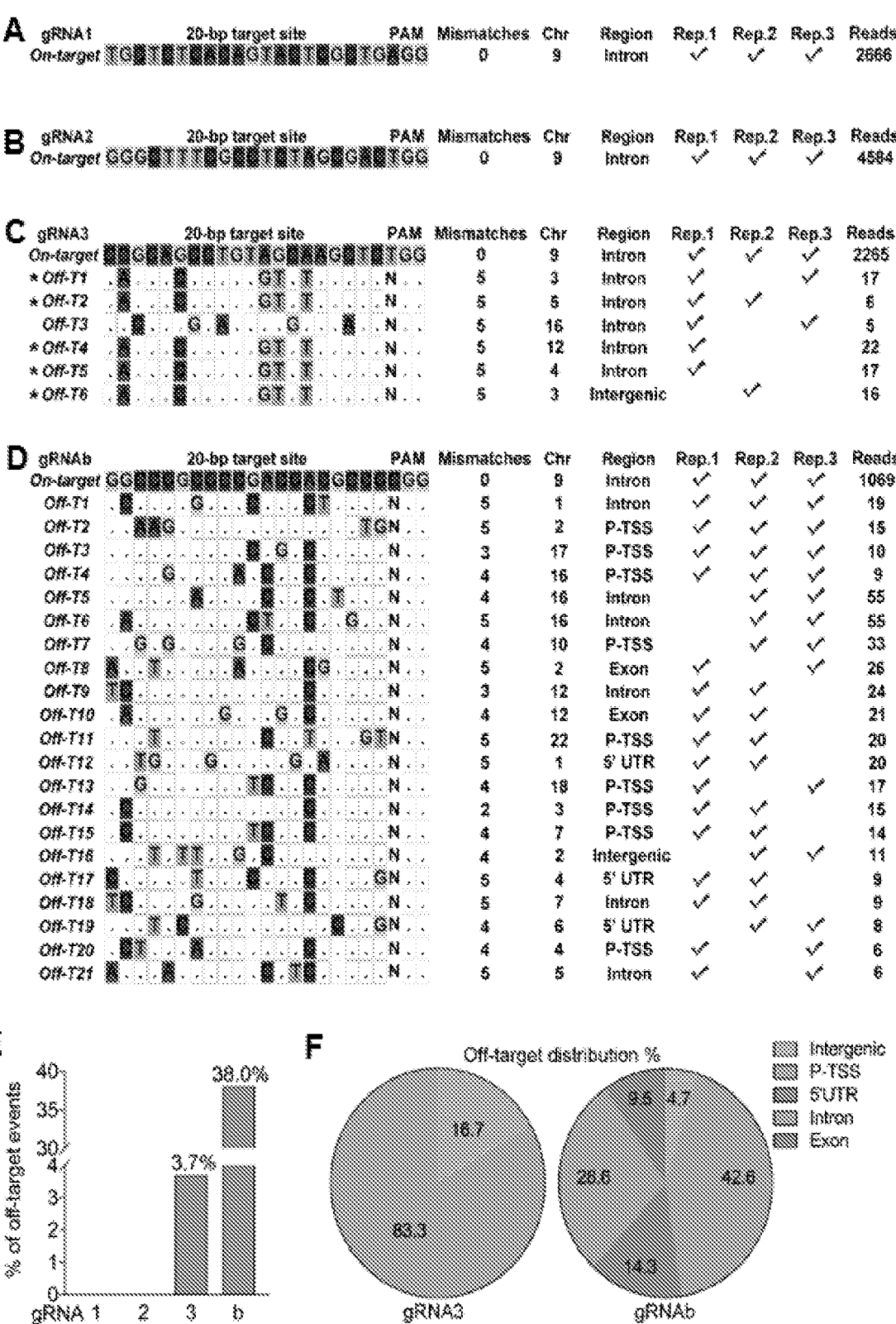

(B) All available gRNAs lie between the repeat site and exon 1b (Ex1b). The gRNAb is in antisense orientation, and the rest of gRNAs are in sense orientation;

(C) Off-target summary of gRNAs we examined (https://portals.broadinstitute.org/gpp/public/analysis-tools/sgrna-design). The off-target details are shown in Table 1;

(D) Genomic DNA PCR for detecting the removal of repeat site by gRNA1-2 and gRNA3-b. The HEK293 cells constitutively expressing Cas9 were infected with the lentiviral control, gRNA1-2, and gRNA3-b, respectively. The repeat site deletion or repeat site plus exon1b (E1b) deletion (A) appeared in cells infected with gRNA3-b and gRNA1-2, respectively. Due to the high GC content at the repeat site, amplicons with repeat site did not appear in control group under the same PCR conditions. The amplicons of C9ORF72 last exon were used for PCR reaction control. The primers used here were illustrated in FIGS. 1A; (E and F) The repeat deletion bands (A) shown in (D) were applied for both forward and reverse Sanger sequencing. The editing site fusions took place upstream of the PAM sites;

FIG. 2 shows no detectable off-target effect of gRNA1-2 measured by GUIDE-seq, wherein (A-D) Off-target sites identified by GUIDE-seq. Mismatches are shaded. In C, asterisks indicate that the same off target sequences in different chromosomes (E) Off-target percentage was estimated by ratio of off-target reads to on-target reads detected by GUIDE-seq;

(F) Off-target site distribution of gRNA3 and gRNAb. In A-D, mismatches in protospacer are no more than 5. P-TSS, region between promoter and TSS (transcription start site). 5'UTR, 5' untranslated region.

Figure 3:
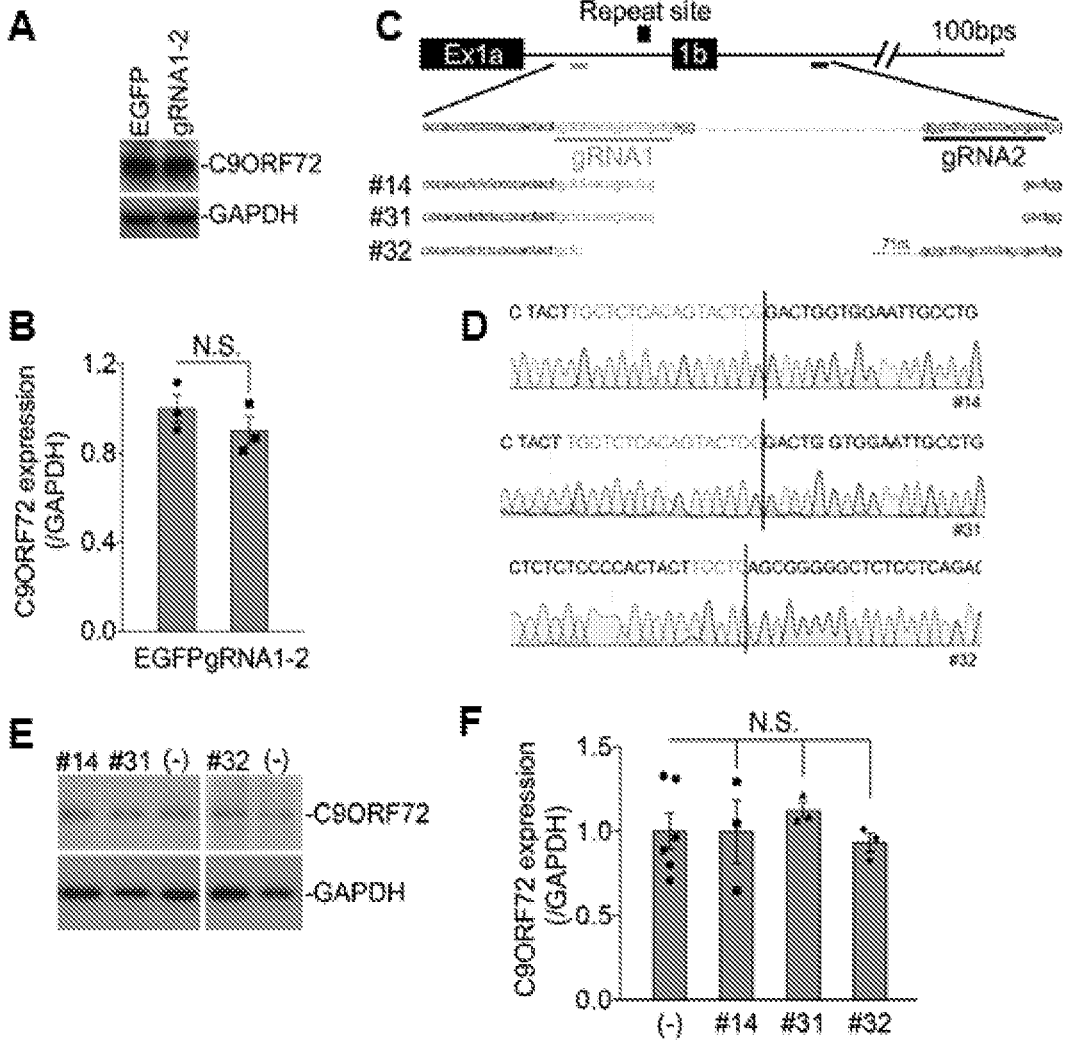

FIG. 3 shows the gRNA1-2-mediated deletion of repeat site and exon 1b has little effect on C9ORF72 expression, wherein (A) Representative image of C9ORF72 immunoblot from HEK293 cells infected with control (EGFP) or gRNA1-2 lentiviral particles. GAPDH serves as loading control. The HEK293 cells were constitutively expressed Cas9;

(B) Relative expression level of C9ORF72 (normalized to GAPDH) shown in A;

(C) Three individual single clone cell lines (#14, 31, and 32) with the repeat site and exon 1b deletion. Sequence alignment shows the deleted regions in these three lines;

(D) The deletion in these lines was confirmed by the Sanger sequencing;

(E) Representative images of C9ORF72 immunoblot from the control (−) and #14, 31, and 32 lines;

(F) Statistic analysis of C9ORF72 relative expression level shown in E. In B and F, the values are presented as mean±SEM (n≥3). N.S., no significance (t-test or ANOVA, SPSS).

Figure 4:
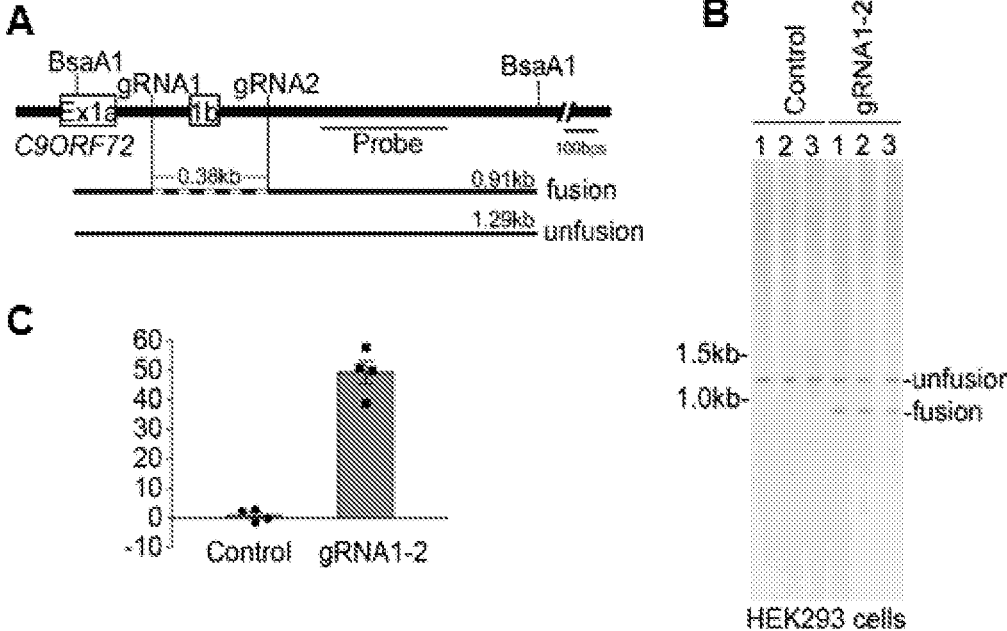

FIG. 4 shows the fusion efficiency of gRNA1-2 editing sites in the HEK293 cells, wherein (A) The experimental design for detecting the fusion efficiency by Southern blot. The BsaA1 enzyme was used to fragment the genomic DNA. The Southern blot probe is set downstream of the gRNA2;

(B) Genomic DNA from the HEK293 cells infected with control and gRNA1-2 lentivirus was applied for the Southern blot. The fusion bands are present in the gRNA1-2 infected cells but not the controls;

(C) The fusion efficiency was estimated by the ratio of fusion to total (fusion+unfusion) band density. The values are presented as mean±SEM (n=4).

Figure 5:
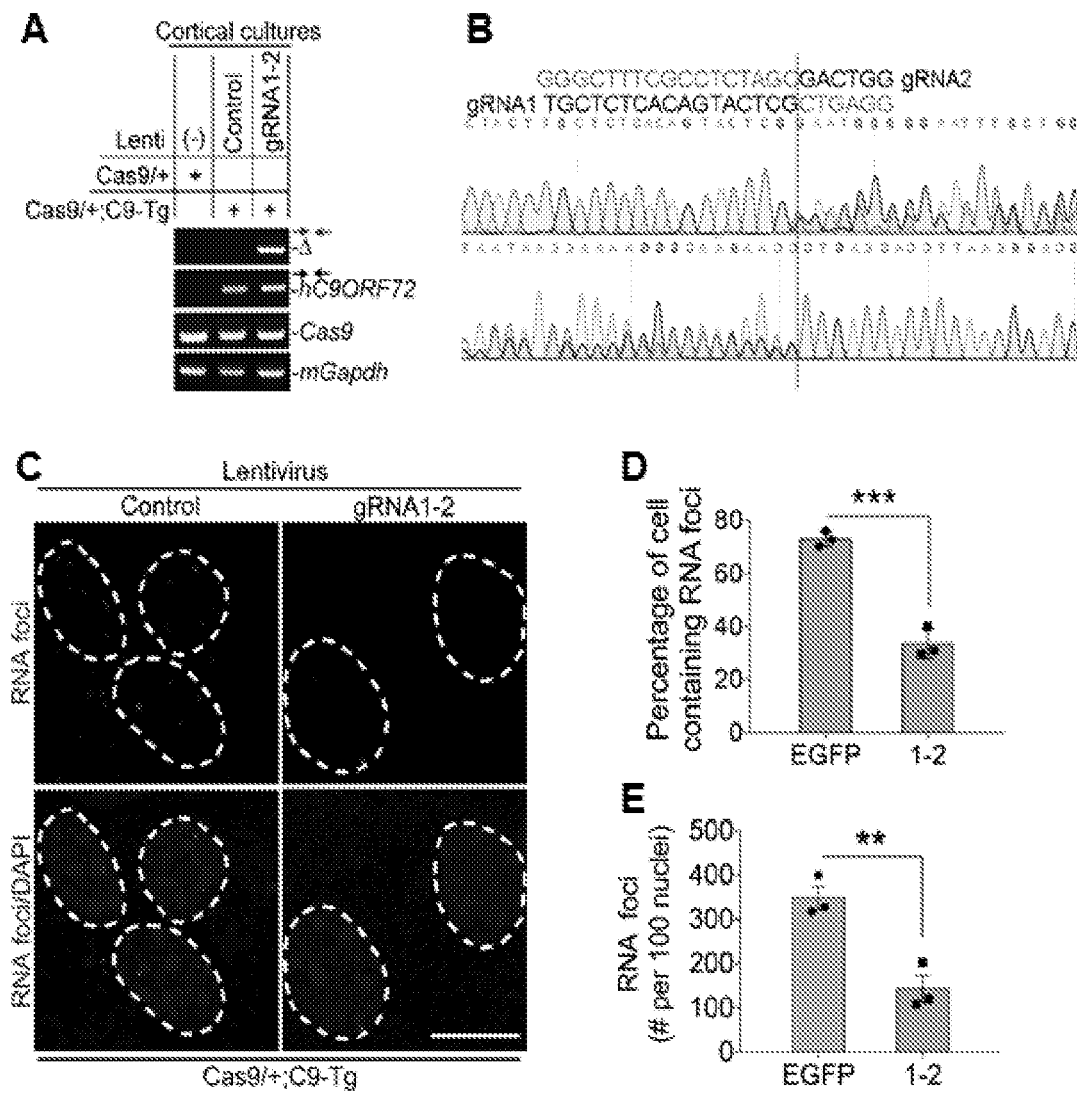

FIG. 5 shows the inventor's designed gRNA1-2 remove the C9ORF72 repeat expansion and correct the C9ORF72 RNA foci in primary cortical cultures, wherein (A) The primary cortical cultures derived from Cas9/+ or Cas9/+; C9-Tg mice were infected with control and dual-gRNA (1-2) lentiviral particles. The Cas9/+ mouse constitutively expresses Cas9 (PMID: 25263330) and the C9ORF72-BAC transgenic mouse (C9-Tg) carries the expanded GGGGCC repeats from patient (C9-Tg mouse line 112, PMID: 26637796). The editing site fusions (A) were detected by primers shown in FIG. 1A;

(B) The repeat deletion band (A) shown in (A) was applied for both forward and reverse Sanger sequencing. The editing site fusions took place upstream of the PAM sites;

(C-E) gRNA1-2 significantly reduced the RNA foci produced by the C9ORF72 repeats in the primary cortical cultures derived from Cas9/+; C9-Tg mice. Control, control lentiviral particles.

Figure 6:
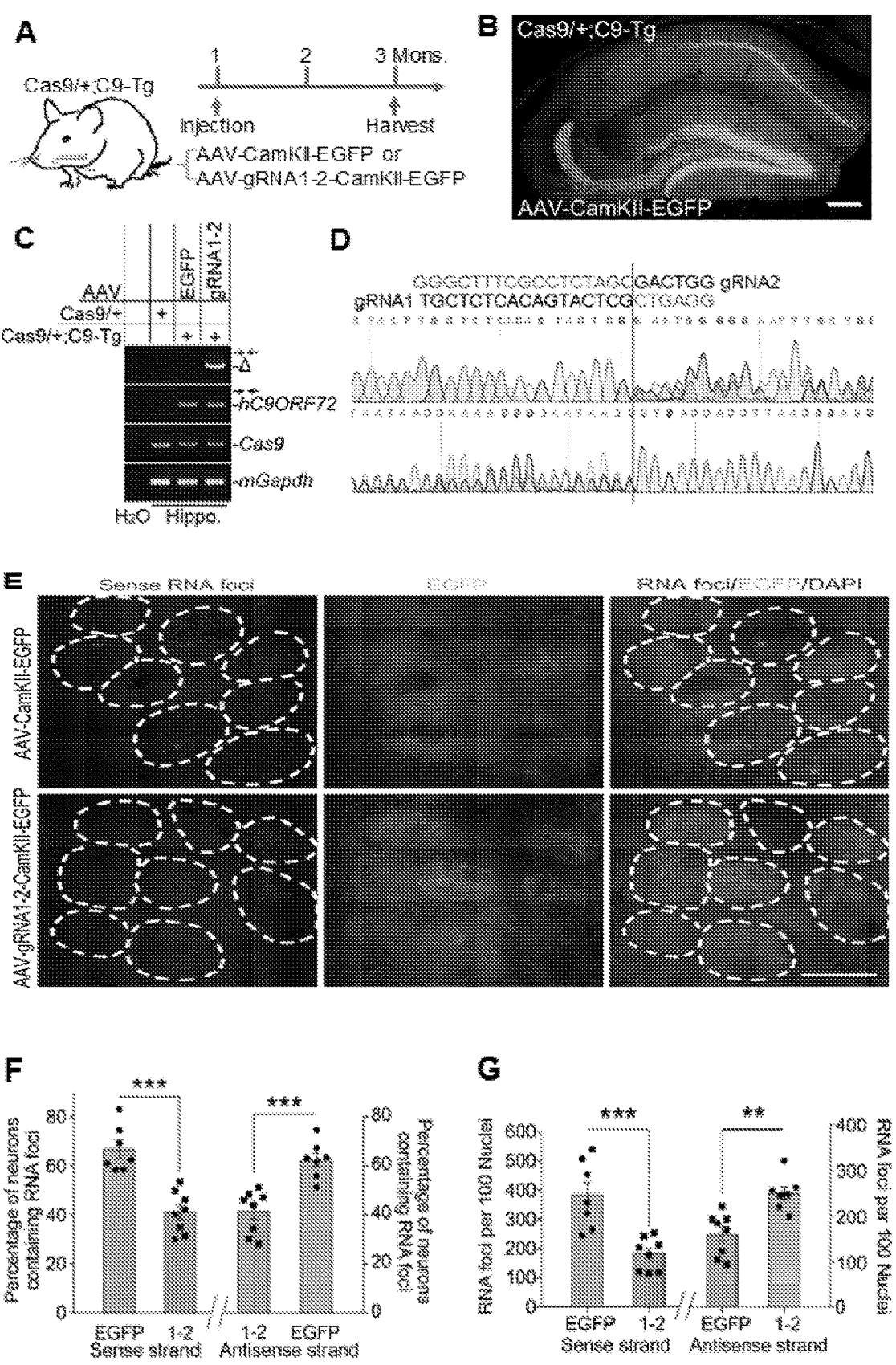

Both the percentage of cells containing foci (D) and the total numbers of foci per 100 cells (E) were significantly reduced in dual-gRNA treatment groups. The values (D and E) are presented as mean±SEM (n=3). ***p<0.001 (t-test, SPSS). Scale bar in (C), 10 FIG. 6 shows AAV-based dual gRNA1-2 remove the C9ORF72 repeats and correct both sense and antisense RNA foci in vivo, wherein (A) The experimental procedure for removal of the C9ORF72 repeats in vivo. The AAV-CamKII-EGFP or AAV-gRNA1-2-CamKII-EGFP was injected into hippocampi of the Cas9/+; C9-Tg mice at one month of age and the infected hippocampi were harvested two months after injection;

(B) The representative image of hippocampus injected with AAV-CamKII-EGFP;

(C and D) The band (Δ) of fusion at two editing sites only appeared in the hippocampus of the Cas9/+; C9-Tg mouse injected with AAV-gRNA1-2-CamKII-EGFP (gRNA1-2) but not in that with AAV-CamKII-EGFP (EGFP). The band (Δ) shown in (C) was applied for

6 both forward and reverse Sanger sequencing (D). The editing site fusions were confirmed at the upstream of the PAM sites;

(E) The AAV-CamKII-EGFP- or AAV-gRNA1-2-CamKII-EGFP-infected hippocampal CA1 regions were applied for the RNA foci measurement. The AAV-mediated EGFP expression was used to trace the infected region and neurons; (F and G) The percentage of infected neurons containing the RNA foci (F) and the total numbers of foci per 100 EGFP-positive cells (G) were measured. For RNA foci detection, AAV-CamKII-EGFP (n=7), AAV-gRNA1-2-CamKII-EGFP (n=8). In F and G, the values are presented as mean±SEM.  p<0.01, *p<0.001 (t-test, SPSS). Scale bar in B, 200 μm; in E, 10 μm.

DETAILED DESCRIPTION OF THE EMBODIMENTS

Identification of the expanded GGGGCC repeats of C9ORF72 in both ALS (Amyotrophic lateral sclerosis) and FTD (frontotemporal dementia) provides genetic basis for the pathogenic and pathological overlaps between the two distinct neurodegenerative disorders (DeJesus-Hernandez et al., 2011; Renton et al., 2014; Renton et al., 2011). The hexanucleotide repeats have explained a large proportion of ALS and FTD cases, including both familiar and sporadic ALS and FTD (Renton et al., 2014), underscoring the critical role of the expanded repeats in the pathogenesis.

At DNA level, the repeat expansion forms abnormal nucleotide structures, such as G-quadruplexes, which increase local genome instability and cause haploinsufficiency in C9ORF72 expression (Belzil et al., 2013; DeJesus-Hernandez et al., 2011; Xi et al., 2013). Indeed, low level of C9orf72 protein leads to immune dysregulation, which has been associated with pathogenesis of many neurodegenerative diseases (Burberry et al., 2016; O'Rourke et al., 2016). At RNA level, the expanded GGGGCC repeats are bidirectionally transcribed into repeat RNAs, which form sense and antisense RNA foci to sequester RNA binding proteins (RBPs) and disturb normal functions of these RBPs (DeJesus-Hernandez et al., 2011; Gendron et al., 2013; Mori et al., 2013a). At protein level, dipeptide repeat (DPR) proteins generated from repeat-associated non-ATG (RAN) translation contribute to the disease pathogenesis by impairing stress granule phase separation, nuclear pore protein trafficking, and heterochromatin structure (Ash et al., 2013; Freibaum et al., 2015; Gendron et al., 2013; Lee et al., 2016; Mori et al., 2013b; Taylor et al., 2016; Zhang et al., 2015; Zhang et al., 2018; Zhang et al., 2016; Zhang et al., 2019; Zu et al., 2013). Currently, no therapeutic design is available to target the GGGGCC repeat-mediated toxicities at DNA, RNA, and protein levels at a time.

With the advances of genome editing approaches, especially the CRISPR/Cas9 technology, it becomes possible to correct the genetic mutations devastating to human health (Komor et al., 2017; Pickar-Oliver and Gersbach, 2019; Wright et al., 2016). Using dual-gRNA-mediated deletion, the mutant exon of dystrophin in Duchenne muscular dystrophy (DMD) was removed and the muscle functions were partially restored (Long et al., 2016; Nelson et al., 2016; Tabebordbar et al., 2016).

The intronic location of C9ORF72 repeat expansion makes it suitable for dual-gRNA-mediated mutant site removal and limits generation of additional out-of-frame mutation often introduced by exonic editing. However, low complexity of DNA region neighboring GGGGCC repeat site makes it almost impossible to select high quality gRNA with low off-target effect but keep the C9ORF72 transcript intact. Here, we selected two intronic gRNAs surrounding the C9ORF72 repeat expansion outside of the low complexity DNA region, which remove the repeat site together with a non-coding exon (exon 1b) of C9ORF72. Using a super sensitive and genome-wide off-target detector, we demonstrated that, indeed, the dual gRNAs we choose have no detectable off-target effect, but gRNA in the low complexity DNA region has high detectable off-target percentage (38%). In addition to no detectable off-target effect, the dual gRNAs we selected have a high repeat DNA removal efficiency (~50%) but have little effect on C9ORF72 protein expression. In neurons carrying human C9ORF72 repeat expansion, the dual gRNAs remove repeat expansion in vitro and in vivo. In consistent with ~50% repeat DNA removal efficiency, the dual gRNAs with high efficacy correct repeat expansion-generated RNA foci, a pathological hallmark shown in patients, in vitro and in vivo. Therefore, we provide a one-time treatment solution here to permanently remove the repeat DNA expansion with high efficiency, which potentially corrects the repeat-mediated RNA and protein abnormalities at the same time.

Our solution could have therapeutic value to treat ALS and FTD patients carrying the C9ORF72 repeat expansion.

The aforementioned features and advantages of the invention as well as additional features and advantages thereof will be more clearly understood hereafter as a result of a detailed description of the following embodiments when taken conjunction with the drawings.

The embodiments described herein with reference to drawings are explanatory, illustrative, and used to generally understand the present invention. The embodiments shall not be construed to limit the scope of the present invention. The same or similar elements and the elements having same or similar functions are denoted by like reference numerals throughout the descriptions.

Materials and Methods

Cell Culture

Primary cortical cultures were prepared from postnatal mouse pups. As previously described (O'Rourke et al., 2015), the cortex was cut into small pieces and digested at 37° C. for 15 minutes. To stop digestion, the complete medium (DMEM supplemented with 10% FBS) was applied. After digestion, the tissue suspension was filtered with a 40-μm cell strainer (Falcon) and centrifuged at 1000×g for 8 minutes. Cells were counted with cell counting equipment and seeded in 24-well plate at 37° C. with 5% $CO_2$. After 4-hour incubation, the culture medium was removed and replaced with maintenance medium, containing Neurobasal (Gibco), B27 (Invitrogen), and glutamine (Invitrogen). Anti-Tuj-1 (1; 1000 mouse, Beyotime, China) immunostaining was used for characterization of the cultured neurons. HEK293, U251, and SH-SY5Y cells were grown in DMEM supplemented with 10% FBS at 37° C. with 5% $CO_2$. For selecting the single clone cells, lentiviral infected cells were placed in 96-well plate by glass micropipette (Sutter Instrument). The genotypes of single clone cell lines were characterized by PCR and sanger sequencing.

Lentiviral Infection.

To generate lentiviral particles expressing dual gRNAs, we inserted an additional H1 promoter into lentiCRISPR V2 (Addgene 52961) to drive the second gRNA expression. To track the lentiviral infected cells, we modified lentiCRISPR V2 by replacement of Cas9 with EGFP. For constitutively expressing Cas9, we employed lentiCas9-Blast (Addgene 52962). For virus packaging, HEK293FT cells were co-transfected with the lentiviral plasmids, pCMV-VSV-G (Addgene 8454), and psPAX2 (Addgene 12260) by polyethyleneimine (PEI) (Polysciences 23966). 72 hours after transfection, the cell culture medium was collected and ultracentifuged, and the pellet was resuspended overnight at 4° C. Cells were infected with lentiviral particles for 48 hours. If necessary, antibiotic selection was carried out to remove the uninfected cells.

RNA Foci Detection In Vitro and In Vivo.

For RNA foci detection, we employed locked nucleic acid (LNA) DNA probes (sense probe, TYE563-CCCCGGCCCCGGCCCC; antisense probe, TYE563-GGGGCCGGGGCCGGGG, Exiqon, Inc.), and performed the in situ hybridization under a RNase-free condition as described previously (Jiang et al., 2016; Liu et al., 2016; O'Rourke et al., 2015).

For RNA foci detection in vitro, primary cortical cultures were prepared from P8 pups. After 12 days in vitro (DIV12) culture, the cells on the coverslip were fixed and permeabilized with 4% PFA and 0.3% Triton X-100 at room temperature for an hour. The cells were incubated with hybridization buffer, which contain 50% formamide (Biotopped), EDTA-2×SSC (Sigma-Aldrich), 300 mM sodium chloride (pH 7.0), and 10% dextran sulfate (Biotopped), at 66° C. for an hour. After pre-hybridization, the cells were hybridized with the LNA probe (40 nM) at 66° C. for 5 hours. After hybridization, the coverslips were washed with 2×SCC in 0.1% Tween-20 at room temperature once and washed with 0.1×SCC at 65° C. for three times. RNA foci quantification was performed as previously described (Jiang et al., 2016; Liu et al., 2016; O'Rourke et al., 2015). For percentage of cell containing RNA foci, we only included the cells containing more than one RNA focus.

For RNA foci detection in vivo, mouse brains were fixed in 4% PFA (pH 7.4) and then embedded in OTC (Sakura Tissue Tek). The frozen sections were processed with longer hybridization time. The auto-fluorescence of lipofuscin in brain sections were quenched by Sudan Black B (Sigma).

Mouse.

C9ORF72-BAC transgenic mice (C9-Tg, Stock No. 023099 at JAX) were originally imported from The Jackson Laboratory and crossed to Rosa26-Cas9 knockin mice (JAX, Stock No. 024858) which are constitutively expressing Cas9 endonuclease. The animal facility at Tsinghua university has been fully accredited by the Association for the Assessment and Accreditation of Laboratory Animal Care International (AAALAC) since 2014. All animal protocols were approved by the Institutional Animal Care and Use Committee (IACUC) at Tsinghua university based on Guide for the Care and use of Laboratory Animals (Eighth Edition, NHR).

Dual-gRNA Delivery In Vivo.

To generate recombinant adeno-associated (rAAV) particles expressing dual gRNAs, we inserted U6 and H1 promoters into pAAV-CaMKII-EGFP (Addgene 50469) to generate pAAV-gRNA1-2-CamKII-EGFP to drive the dual-gRNA expression. For rAAV packaging, the AAV plasmids were co-transfected with helper plasmids into HEK293T cells by PEI. The cells were harvested and lysed with lysis buffer, which contains 150 mM sodium chloride, 20 mM Tris-Hcl (pH=8), 5% sodium deoxycholate (sigma), and 50 U/ml Benzonase endonuclease (sigma). The viral particles were purified with HiTrap Heparin column (Sigma) and the titer was determined by real-time quantitative PCR. For dual-gRNA delivery in vivo, rAAV (>5.0×10$^{12}$ genome copies/ml) was stereotaxically injected into mouse hippocampal CA1 region at 1-month of age. Two months after injection, the brains were harvested for RNA foci measurement.

Immunostaining and Immunoblot

For immunostaining, primary cortical cultures were fixed with 4% PFA at room temperature for 15 minutes. The cells were blocked with 0.3% BSA/Triton X-100 at room temperature for 60 minutes, and then were incubated with the primary antibody (anti-Tuj-1, Beyotime) at 4° C. overnight. Alexa Fluor conjugated secondary antibody (ThermoFisher) was applied at room temperature for 60 minutes. The florescent images were captured by Leica confocal microscopy.

For immunoblot, cells were lysed in RIPA buffer (50 mM Tris-HCl, pH 8.0, 150 mM NaCl, 0.25% sodium deoxycholate, 0.1% SDS, 1% NP-40, supplemented with complete protease inhibitor mixture). Blots were incubated with anti-C9orf72 antibody (ProteinTech 66140-1) overnight at 4° C. and then HRP-conjugated secondary antibody. The band intensities were calculated by Fiji ImageJ.

Southern Blot

Figure 1:
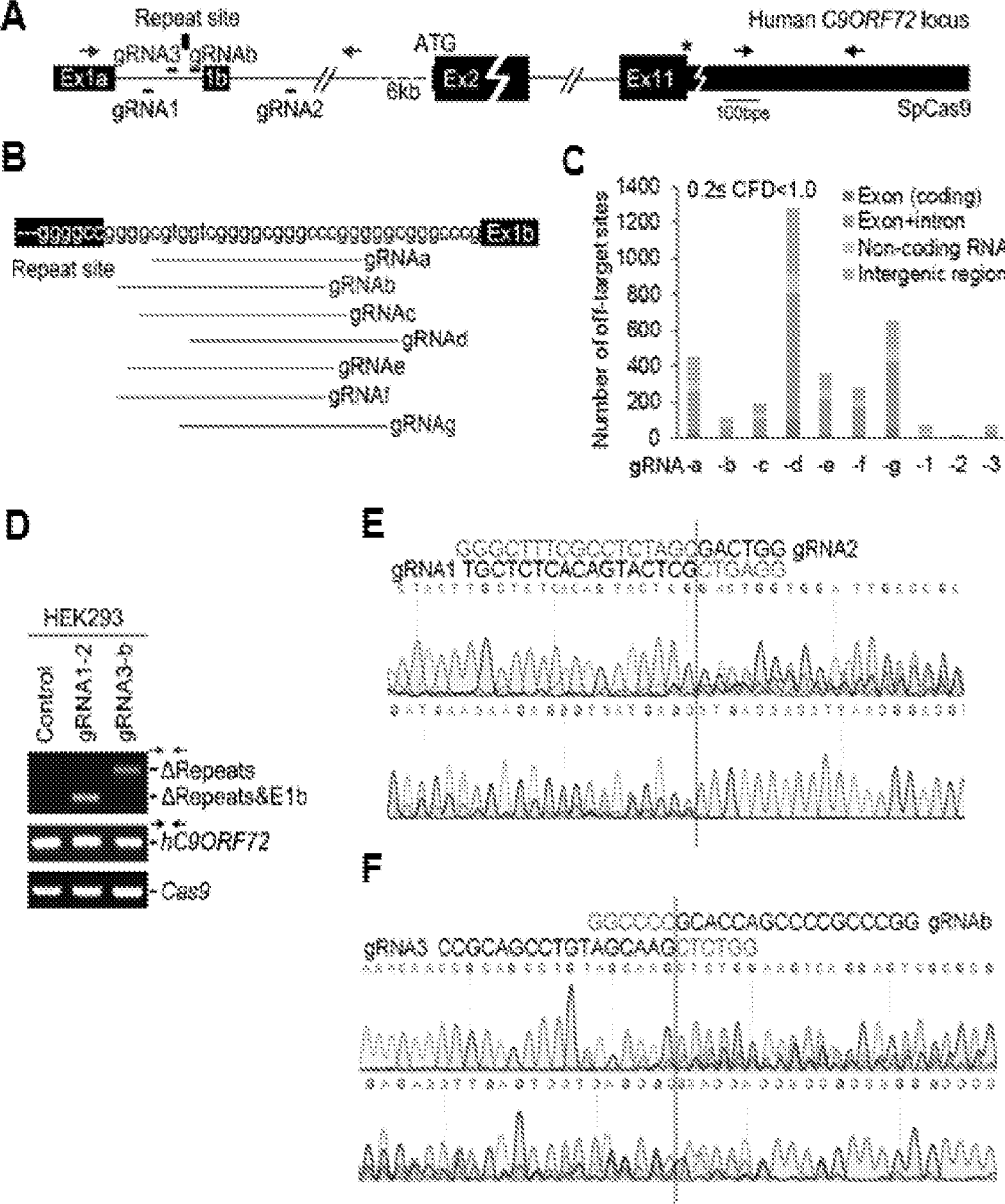
FIG. 1 shows the inventor's designed dual gRNAs remove the C9ORF72 repeat site in human cells, wherein (A) The human C9ORF72 genome structure and our dual-gRNA design (gRNA1 and 2 or gRNA 3 and b) for removal of the C9ORF72 repeat site. The gRNAs described here are SpCas9-based. The primers flanking the gRNA editing sites labeled as black arrows were used for genotyping the removal. The primers in last exon (exon 11, Ex11) labeled as black arrows were used for detecting human C9ORF72.

Genomic DNA (50 μg) from HEK293 cells infected with dual-gRNA lentivirus was digested overnight with the restriction endonucleases, and DNA fragments were sepa- 36-bp upstream of exon 1b, consistent with the previous repeat site description (FIG. 1A) (DeJesus-Hernandez et al., 2011; Renton et al., 2011). In agreement with two online gRNA designers (Haeussler et al., 2016; Hsu et al., 2013), gRNAs (gRNA1 and gRNA3) in the 173-bp region between the exon 1a and the repeat site were identified as two upstream gRNAs with the low predicted off-target effect (FIG. 1A and Table 1). For downstream gRNA, the ideal location is in the 36-bp region between repeat site and exon 1b, which pairs with the upstream gRNA to remove the repeat expansion without disturbing the exon 1b. However, the 36-bp region is a low complexity region and all the gRNAs identified in this 36-bp region have high predicted off-target effect. Among them, gRNAb was scored the best (FIG. 1B, 1C, and Table 1). In order to avoid the potential off-target effect of downstream gRNA, we sought DNA region downstream of exon 1b and found gRNA2, which is close to exon 1b and has low predicted off-target effect (FIG. 1A, 1C, and Table 1). Therefore, we ended up with two designs: 1) gRNA1 and gRNA2 pair (gRNA1-2), which removes the repeat site together with the exon 1b with low predicted off-target effect; 2) gRNA3 and gRNAb pair (gRNA3-b), which removes the repeat site and keeps the exon 1b intact (FIG. 1A).

TABLE 1

Off-target analysis of gRNAs for removal of C9orf72 repeat expansion.

| gRNA | Up-/down-stream of Ex1b | Score* | Exon (coding) | Exon + intron | Non-coding RNA | intergenic region | Total number of off-target sites |
|---|---|---|---|---|---|---|---|
| a | Downstream | 63 | 38 | 225 | 45 | 143 | 451 |
| b | Downstream | 64 | 14 | 52 | 13 | 33 | 112 |
| c | Downstream | 62 | 17 | 98 | 23 | 56 | 194 |
| d | Downstream | 40 | 107 | 700 | 103 | 370 | 1280 |
| e | Downstream | 50 | 29 | 192 | 46 | 94 | 361 |
| f | Downstream | 43 | 20 | 158 | 34 | 71 | 283 |
| g | Downstream | 29 | 58 | 370 | 63 | 166 | 657 |
| 1 | Upstream | 82 | 4 | 19 | 11 | 37 | 71 |
| 2 | Downstream | 96 | 1 | 12 | 0 | 6 | 19 |
| 3 | Upstream | 76 | 1 | 38 | 11 | 26 | 76 |

Note:

The online off-target predication programs employed for high scored gRNAs.

*the score given by the CRISPR design (http://crispr.mit.edu/).

The off-target sites were predicted by sgRNA Designer (http://portals.broadinstitute.org/gpp/public/analysis-tools/sgrna-design).

The CFD (Cutting Frequency Determination) score we used between 0.2 to 1.0 (0.2 ≤ CFD < 1.0).

rated by agarose gel. The DNA was then transferred onto Hybond-N+ membrane (Amersham) by capillary equipment with 20×SSC (30 mM sodium citrate and 300 mM sodium chloride, pH 7.0). Hybridization was performed in Church-Gilbert buffer (7% [w/v] SDS, 10 mM EDTA and 0.5 M phosphate buffer, pH 7.2) at 65° C. overnight with [α-$^{32}$P]-labeled (Perkin-Elmer) DNA probe (Rediprime II System, Amersham). The membrane was washed with 2×SSC and 0.1% SDS twice at 65° C. for 20 min each, and then washed with 1×SSC and 0.1% SDS for 20 min. Signals were developed on X-ray film for 3 days at −70° C. The band intensities were calculated by Fiji ImageJ.

GUIDE-Seq and Data Analysis

GUIDE-seq library construction and data analysis were performed as previously described (Tsai et al., 2015).

Results:

Our Design for Removal of Human C9ORF72 Repeat Site.

In order to remove the expanded GGGGCC repeats in the intron of C9ORF72, we analyzed the genomic sequences of human C9ORF72 (FIG. 1A). Three times of GGGGCC (repeat site) are found 173-bp downstream of exon 1a and Our Designed Dual gRNAs Remove C9ORF72 Repeat Site in Human Cells.

To test our designs, we employed human HEK293 cell constitutively expressing Cas9 and ensured our gRNA target sequences present in the genomic DNA. Besides HEK293 cell, the target sequences of gRNA1, 2, and b are present in the other 11 human cell lines we examined. We noticed a SNP (single nucleotide polymorphism) in gRNA3 target sequences in 3 out of 12 human cell lines we examined, suggesting a SNP hot spot in the target sequences, which may need additional design for future precise editing.

To express two gRNAs in the same cell with high chance, we combined previously reported dual-gRNA expression and lentiviral delivery systems (Aparicio-Prat et al., 2015; Sanjana et al., 2014) Indeed, the editing site fusion appeared in the HEK293 cells infected with lentiviral particles expressing gRNA1-2 or gRNA3-b but not empty control (FIG. 1D). The fusion took place at the Cas9 cutting sites, further confirming that the repeat site deletion is mediated by our dual gRNAs (FIGS. 1E and 1F). Therefore, we concluded that our approach is able to remove C9ORF72 repeat site in human cells.

No Detectable Off-Target Effect of gRNA1-2 Measured by GUIDE-Seq.

Given that off-target effect introduced by CRISPR/Cas9 is a major risk factor for its application on human disease therapy (Akcakaya et al., 2018; Komor et al., 2017; Pickar-Oliver and Gersbach, 2019; Tsai et al., 2015; Wright et al., 2016), limited off-target effect of the gRNA is essential for its future application. To identify potential off-target sites of our selected gRNAs, we employed both computational prediction and experimental identification approaches. In agreement with other online off-target predictors (Table 1), Cas-OFFinder, a fast and versatile algorithm (Bae et al., 2014), predicted much more off-targets in gRNA3-b pair than in gRNA1-2 pair when we allowed mismatches in the protospacer region (Table 2).

TABLE 2

Numbers of gRNA1, gRNA2, gRNA3 and gRNAb off target sites predicted by Cas-OFFinder.

| gRNA | Numbers of off-target sites | | | | | | | |
| | 0- | 1- | 2- | 3- | 4- | 5- | 6- | 7-mismatches |
| --- | --- | --- | --- | --- | --- | --- | --- | --- |
| gRNA1 | 1 | 0 | 0 | 9 | 84 | 886 | 6500 | 41248 |
| gRNA2 | 1 | 0 | 0 | 1 | 21 | 326 | 3296 | 24889 |
| gRNA3 | 1 | 0 | 1 | 9 | 135 | 2146 | 7870 | 43595 |
| gRNAb | 1 | 0 | 1 | 43 | 303 | 2004 | 12532 | 59337 |

Note:
The off-target numbers were predicted by Cas-OFFinder (http://www.rgenome.net/cas-offinder/).

To experimentally identify off-target genomic loci of our gRNAs, we employed GUIDE-seq, a unbiased and sensitive genome-wide off-target site identification method (Klein-stiver et al., 2016; Tsai et al., 2015). We delivered our gRNAs and the oligodeoxynucleotide (dsODN) that incor-porates into cutting site induced by Cas9 into HEK293 cells constitutively expressing Cas9. Indeed, thousand unique reads from three individual experiments support on-target integration of dsODN of each one of our gRNA by GUIDE-seq (FIG. 2A-2D), which was further confirmed by genomic DNA PCR. To ensure off-target events detected by GUIDE-seq are reliable, we only included the events that were supported by more than 5 unique reads from at least two out of our three independent experiments (FIG. 2A-2D). In contrast to high off-target effect of gRNA3 (3.7%) and gRNAb (38.0%) identified by GUIDE-seq (FIG. 2C-2E), no reliable off-target event was detected in the cells expressing gRNA1 and gRNA2 (FIGS. 2A, 2B, and 2E). For gRNA3 off-target sites, a majority of them (83.3%) locate in the introns and the rest of them (16.7%) are in the intergenic region (FIG. 2F). In contrast, because the target sequences of gRNAb are GC-rich, many its off-target sites locate in the region between promoter and TSS (P-TSS, 42.6%) and 5'UTR (14.3%). Some gRNAb off-target sites hit protein coding exons (9.5%), suggesting that the off-target effect of gRNAb leads to functional impairments of these off-target genes. Taken together, our online prediction and experimen-tal results support no detectable off-target effect of our gRNA1-2 design, but the high off-target effect of gRNAb, which may limit its future clinical application.

The Deletion of Repeat Site Together with Exon 1b by gRNA1-2 has Little Effect on C9ORF72 Expression.

Haploinsufficiency of C9ORF72 in C9-ALS/FTD patients implies that loss-of-function of C9ORF72 may contribute to disease pathogenesis (DeJesus-Hernandez et al., 2011; Renton et al., 2011). In addition, C9orf72 deficient mice showed abnormal immune response (Atanasio et al., 2016;

Burberry et al., 2016; O'Rourke et al., 2016). Given that our gRNA1-2 design removes both the repeat site and exon 1b, we then asked whether the removal affects the C9ORF72 expression. Using a validated C9ORF72 antibody, we dem-onstrated that the C9ORF72 expression level had no sig-nificant change in HEK293 cells infected with gRNA1-2, compared to non-editing control (FIGS. 3A and 3B). To examine whether our designed gRNAs affects C9ORF72 expression in cells derived from human brain, we employed U251, a human glioblastoma line, and SH-SY5Y, a human neuroblastoma line. Like in HEK293 cell, our gRNA1-2 removed the repeat site in these two cell lines constitutively expressing Cas9. In agreement with the results seen in HEK293 cells, the dual gRNAs do not change the C9ORF72 expression. To further confirm that gRNA1-2 has little effect on C9ORF72 expression, we established three independent HEK293 single clones which were absent of the repeat site and exon 1b (FIGS. 3C and 3D). In comparison with the non-editing control, no significant C9ORF72 expression level change was shown in these single clone cell lines (FIGS. 3E and 3F). Together, these results indicated that removal of repeat site and exon 1b by our dual gRNA1-2 has little effect on C9ORF72 expression in human cell lines derived from human brain and non-neuronal tissue.

Our gRNA1-2 Lead to High Fusion Efficiency at their Editing Sites.

The removal of repeat expansion depends on the fusion of the gRNA1 and 2 editing sites. Therefore, high fusion efficiency will lead to high chance of repeat expansion removal and better therapeutic outcome. To examine the fusion efficiency, we infected HEK293 cells constitutively expressing Cas9 with dual gRNA1-2 lentiviral particles and performed Southern blot (FIGS. 4A and 4B). The unfusion bands appeared in both cells infected with control or dual-gRNA lentiviral particles. However, the fusion band only appeared in the cells infected with dual gRNA1-2. These results demonstrated that the fusion results from dual-gRNA-mediated editing, which does not always lead to fusion. Next, we calculated the fusion efficiency by mea-suring the ratio of fusion to total band intensity, and revealed that the repeat site removal efficiency reached to 49.5±5.8% (FIG. 4C). Therefore, we concluded that our designed gRNA1-2 leads to about 50% fusion at their editing sites.

Our Designed Dual gRNAs Remove C9ORF72 Repeat Expansion and Correct the Repeat-Produced RNA Foci in Primary Cortical Cultures.

To examine whether our dual-gRNA strategy is able to remove patient expanded GGGGCC repeats from neuron, we cultured the cortical neurons derived from C9ORF72-BAC (C9-Tg) transgenic mouse (line 112), which carries 100-1000 repeat expansion in size (O'Rourke et al., 2015). The existence of our gRNA1-2 target sequences was con-firmed in the C9-Tg but not in the non-transgenic mice, indicating that the target sequences came from the BAC C9ORF72 transgene. We then crossed the C9-Tg mouse with Rosa26-Cas9 knock-in mouse (Platt et al., 2014) to ensure constitutive expression of Cas9 in the brain and in its derived neurons. Indeed, the editing site fusion appeared in the primary cultures infected with the lentiviral particles expressing the gRNA1-2 but not empty control (FIG. 5A). Like HEK293 cells, the fusion took place at the Cas9 cutting sites, confirming the removal of repeat expansion by our dual gRNAs (FIG. 5B).

We next investigated whether the pathology produced by the C9ORF72 repeat expansion is able to be corrected by our dual-gRNA approach. Similar to previous report (O'Rourke et al., 2015), RNA foci were detected in the primary cortical cultures derived from C9-Tg but not wild type mice. With ~50% repeat site removal efficiency by gRNA1-2 (FIG. 4) and our near hundred percent lentiviral infection rate in our primary cultures, we expected to see ~50% foci correction efficacy in these infected primary cultures. Indeed, half of foci were corrected by expression of gRNA1-2, which was evidenced by the percentage of cells containing the foci and the numbers of foci in the given cells (FIG. 5D-5E). Therefore, we concluded that our approach is able to remove the C9ORF72 repeat expansion and correct the repeat-produced RNA foci, one of the molecular disease hallmarks, in the primary cortical cultures carrying patient repeat expansion. Dual gRNA1-2 Remove C9ORF72 Repeat Expansion and Correct the Repeat-Produced RNA Foci in C9-Tg Brain.

With limited off-target effect, little effect on C9ORF72 expression, high fusion efficiency, and high RNA foci correction efficacy in vitro, we next asked whether our dual gRNA1-2 is able to correct repeat-produced pathology in vivo. In agreement with previous report (O'Rourke et al., 2015), expression of repeat expansion generated widespread sense and antisense RNA foci in hippocampal CA1 pyramidal neurons at both 1- and 3-month old C9-Tg mice but not in that of 3-month old wildtype mice. We then crossed those C9-Tg mice with Rosa26-Cas9 knock-in mice to obtain the offsprings expressing both repeat expansion and Cas9 (FIG. 6A). In these double positive mice, we injected AAV expressing dual gRNA1-2 driven by H1/U6 promoters and EGFP driven by CamKII promoter, a neuronal promoter, which enabled us to monitor the gRNA-targeted neurons (FIG. 6A). The AAV expressing EGFP (AAV-CamKII-EGFP) alone was used as non-editing control. After two month of injection, we achieved high AAV infection efficiency (FIG. 6B) and detected the fusion of gRNA1-2 editing sites in hippocampus infected with AAV-gRNA1-2-CamKII-EGFP, but not AAV-CamKII-EGFP controls (FIG. 6C). Like our editing site fusion in the primary cortical cultures, the in vivo fusion took place at the same Cas9 cutting sites (FIG. 6D). Remarkably, AAV expressing gRNA1-2 significantly decreased the percentage of EGFP-positive neurons containing the sense and antisense RNA foci and the numbers of RNA foci in the EGFP-positive neurons, compared to the AAV-CamKII-EGFP controls (FIG. 6E-6G). Therefore, our results indicate that our dual-gRNA approach is able to remove the repeat expansion and correct the repeat expansion-generated pathology in vivo.

Discussion:

Currently, preclinical treatments for ALS/FTD caused by C9ORF72 repeat expansion are mainly focused on its abnormal RNA, including antisense oligonucleotide (ASO)-based target RNA silencing, microRNA-based silencing, and dCas9-based target RNA editing (Batra et al., 2017; Donnelly et al., 2013; Jiang et al., 2016; Lagier-Tourenne et al., 2013; Peters et al., 2015; Sareen et al., 2013). Those approaches are able to correct RNA foci formed by RNAs transcribed from the GGGGCC repeats. However, the toxic DPR proteins are translated by RAN translation from both antisense and sense repeat RNAs (Ash et al., 2013; Mori et al., 2013b; Zu et al., 2013). It is important for those RNA targeting approaches to consider separate design for targeting both antisense and sense RNAs. Recently, selective reduction of repeat RNA transcription has been emerged as an approach to decrease both antisense and sense RNAs by simply manipulating a single transcription factor (Kramer et al., 2016). However, so far, no available approach is able to treat all three types of toxicities caused by the GGGGCC repeats at DNA, RNA, and protein levels by a simple one-time treatment.

'Cutting-deletion-fusion' mediated by two gRNAs, which removes the DNA sequences between the editing sites, has been shown to successfully rescue the mutant phenotypes in vivo (Long et al., 2016; Nelson et al., 2016; Tabebordbar et al., 2016). The intronic location of C9ORF72 repeat expansion makes it an ideal target for this 'cutting-deletion-fusion' correction mediated by two gRNAs. First, because the editing sites locate in non-coding region of C9ORF72, the editing will not generate out-of-frame mutation. Second, because production of both RNA foci and DPR proteins depends on the repeat DNA expansion, the removal of repeated DNA by our gRNA1-2 potentially correct the repeat-generated RNA and protein toxicities at the same time.

High fusion efficiency at two distal editing sites is important for this 'cutting-deletion-fusion' manipulation (Long et al., 2016; Nelson et al., 2016; Tabebordbar et al., 2016). To achieve it, we employed dual promoters to ensure the two gRNAs expressed in the same cell. Using the Southern blot, we estimated that our gRNA1-2 fusion efficiency is 49.5±5.8% (FIG. 4C). We interpret this result as a sign that cell delivered with our gRNA1-2 and Cas9 will have half chance to have its repeat DNA expansion removed. Because the production of RNA foci and DPR proteins depends on the repeat DNA expansion, we expected relevant efficacy in correction of repeat-caused pathologies. Indeed, our in vitro and in vivo experiments support the efficacy in correction of RNA foci (FIGS. 5C-5E and FIGS. 6E-6G). Due to no DPR protein detected in vitro and much late appearance of DPR protein seen in vivo (O'Rourke et al., 2015), we are unable to examine correction efficacy at protein level. However, we speculate that the DPR production is corrected as well as the RNA foci correction in these edited cells in vitro and in vivo. The high fusion efficiency could have more therapeutic value for non-dividing cell like neuron, because daughter cell inherits genetic modification from parent diving cell after Cas9 editing, if the modification is beneficial for cell viability, which will lead to increased editing efficiency (Long et al., 2016; Nelson et al., 2016; Tabebordbar et al., 2016). For future clinical application, shorter Cas9 from *Staphylococcus aureus* (SaCas9) could be employed (Ran et al., 2015), which allows to pack two gRNAs and SaCas9 in a single AAV particle, to improve in vivo fusion efficiency.

Off-target effect of CRISPR/Cas9 is a major concern for its clinical application (Komor et al., 2017; Pickar-Oliver and Gersbach, 2019; Wright et al., 2016). However, using rational online in silico tools (Bae et al., 2014; Haeussler et al., 2016; Hsu et al., 2013), scientist is able to limit the off-target events (Akcakaya et al., 2018; Kleinstiver et al., 2016; Tsai et al., 2015). The 36-bp DNA sequences between C9ORF72 repeat site and the exon 1b make it almost impossible to select high quality gRNA with low off-target effect but not affecting C9ORF72 transcript integrity. We employed GUIDE-seq, a cell-based super sensitive off-target detector (Tsai et al., 2015), to reveal high off-target rate of gRNAb (38%), which is consistent with our in silico prediction (Table 2). However, no detectable off-target event was identified in cells expressing gRNA1-2 by GUIDE-seq, implicating less off-target concern according to this dual-gRNA future application (FIG. 2). Although our design removes C9ORF72 the repeat site together with noncoding exon 1b, this manipulation has little effect on C9ORF72 protein level in cells derived from human non-neuronal tissue and brain (FIG. 3). Newly-developed an in vitro screen for identifying genome-wide off-target sites could be applied for further interrogation of off-target events of our gRNA1-2 (Akcakaya et al., 2018; Tsai et al., 2017).

Recombinant AAV-mediated gene therapy has been proven in treatment of human spinal muscular atrophy (Wang et al., 2019), underscoring feasibility of AAV-based delivery of gRNA-Cas9 complex into central nerve system (CNS). Alternatively, in vivo efficacy was demonstrated by cationic lipid delivery of gRNA-Cas9 in treatment of hearing loss (Gao et al., 2018). Because high prevalence of exposure to *S. pyogenes* and *S. aureus* in human population, immunogenicity of SpCas9 and SaCas9 is a potential obstacle to its clinical application (Pickar-Oliver and Gersbach, 2019). Identification and characterization of novel Cas9 orthologues with low immunogenicity could be a way to overcome the obstacle. Given that CNS is immune privileged and local application of AAV-based gRNA-Cas9 through intrathecal injection limits whole body immunogenicity (Pickar-Oliver and Gersbach, 2019; Wang et al., 2019), Cas9 immunogenicity could be less concerned according to its CNS application. Controllable expression of Cas9 protein could be also beneficial to avoid the immunogenicity during future clinical application.

Taken together, here we provide a one-time treatment design that can permanently correct DNA repeat expansion, which has high chance to correct RNA and protein abnormalities caused by C9-repeat expansion at the same time. With a half removal efficiency and no detectable off-target effect, the dual-gRNA approach we identified provides therapeutic hope and value for ALS and FTD patients carry the repeat expansion.

It will be apparent to those skilled in the art that variations and modifications of the present invention may be made without departing from the scope or spirit of the present invention. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A group of gRNAs, comprising:

a first gRNA molecule; and a second gRNA molecule capable of defining a region in a genome sequence with the first gRNA molecule, wherein the region in the genome comprises a target sequence in need of removal, wherein the target sequence comprises GGGGCC repeats of C90RF72 gene and that is located between the exon 1a and the exon 1b, wherein the first gRNA molecule is set between the exon 1a and the GGGGCC repeats, the second gRNA molecule is set downstream of the exon 1b but upstream of initiation codon, wherein the first gRNA molecule comprises the nucleic acid sequence of SEQ ID NO: 1; and the second gRNA molecule comprises the nucleic acid sequence of SEQ ID NO: 2.

2. The group of gRNAs of claim 1, wherein the target sequence has at least two GGGGCC repeats.

3. A construct, comprising a sequence encoding the group of gRNAs of claim 1.

4. The construct of claim 3, further comprising:

a first promoter operably linked to a first nucleic acid molecule encoding the first gRNA molecule; and a second promoter operably linked to a second nucleic acid molecule encoding the second gRNA molecule.

5. The construct of claim 4, wherein each of the first and second promoters comprises at least one selected independently from a group consisting of U6, H1, CMV, EF-1, RSV, and LTR promoters.

6. The construct of claim 3, wherein the construct is a virus.

7. The construct of claim 6, wherein the construct is a virus selected from the group consisting of a retrovirus, lentivirus, adenovirus, and adeno-associated virus (AAV).

8. A kit comprising the group of gRNAs of claim 1 and an isolated nucleic acid molecule encoding a nuclease, wherein the nuclease can target a specific genome sequence as a genome editing tool, wherein the nuclease comprises CRISPR/Cas9.

9. A method of modifying a cell in vitro, comprising introducing the group of gRNAs of claim 1 into the cell in need of modification; and introducing a sequence encoding a nuclease, wherein the nuclease can target a specific genome sequence as a genome editing tool, wherein the nuclease can target specific genome sequence as a genome editing tool, and wherein the nuclease comprises CRISPR/Cas9.

10. The method of claim 9, wherein said modifying a cell comprises correcting C9ORF72 repeat expansion for cells.

11. A therapeutic composition for treating C9ORF72 related disease, comprising:

the group of gRNAs of claim 1 and a pharmaceutically acceptable adjuvant.

* * * * *